United States Patent
Fish et al.

(10) Patent No.: US 11,220,469 B2
(45) Date of Patent: Jan. 11, 2022

(54) PROCESSES FOR IMPROVING THE EFFICIENCY OF HYDROCARBON PRODUCTION

(71) Applicant: Dow Global Technologies LLC, Midland, MI (US)

(72) Inventors: Barry B. Fish, Freeport, TX (US); Peter E. Groenendijk, Terneuzen (NL); Davy L. S. Nieskens, Terneuzen (NL); Andrzej Malek, Midland, MI (US); Brien A. Stears, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 1 day.

(21) Appl. No.: 16/754,162

(22) PCT Filed: Oct. 9, 2018

(86) PCT No.: PCT/US2018/054954
§ 371 (c)(1),
(2) Date: Apr. 7, 2020

(87) PCT Pub. No.: WO2019/074894
PCT Pub. Date: Apr. 18, 2019

(65) Prior Publication Data
US 2021/0198164 A1    Jul. 1, 2021

Related U.S. Application Data

(60) Provisional application No. 62/570,325, filed on Oct. 10, 2017.

(51) Int. Cl.
*C07C 1/00* (2006.01)
*C07C 1/04* (2006.01)
(Continued)

(52) U.S. Cl.
CPC .............. *C07C 1/0485* (2013.01); *C01B 3/38* (2013.01); *C07C 4/02* (2013.01); *C07C 5/333* (2013.01);
(Continued)

(58) Field of Classification Search
CPC ........... C07C 11/04; C07C 5/327; C07C 2/84; C07C 11/06; C07C 1/20; C07C 9/04;
(Continued)

(56) References Cited

U.S. PATENT DOCUMENTS

| 6,946,493 B2 | 9/2005 | Mohedas et al. |
| 9,334,204 B1 * | 5/2016 | Radaelli ................ C07C 1/0425 |
| 2011/0112314 A1 | 5/2011 | Chewter et al. |

FOREIGN PATENT DOCUMENTS

| GB | 2444055 B | 5/2008 |
| WO | 2013166369 A1 | 11/2013 |
| WO | 2016007607 A1 | 1/2016 |

OTHER PUBLICATIONS

International Search Report and Written Opinion pertaining to PCT/US2018/054954, dated Jan. 18, 2019.

* cited by examiner

*Primary Examiner* — Sharon Pregler
(74) *Attorney, Agent, or Firm* — Dinsmore & Shohl LLP (57) ABSTRACT

A process for converting a feed stream having carbon to $C_2$ to $C_5$ olefins, includes introducing a feed stream including methane and oxygen to a first reaction zone, reacting the methane and oxygen in the first reaction zone to form a first reaction zone product stream having a mixture of $C_2$ to $C_5$ alkanes, transporting the mixture of $C_2$ to $C_5$ alkanes to a second reaction zone, introducing a fresh stream of at least one of ethane and propane to the second reaction zone, converting the $C_2$ to $C_5$ alkanes to $C_2$ to $C_5$ olefins in the second reaction zone, producing one or more product (Continued)

streams in the second reaction zone, where a sum of the one or more product streams includes $C_2$ to $C_5$ olefins, and producing a recycle stream comprising hydrogen in the second reaction zone, where the recycle stream is transported to the first reaction zone.

16 Claims, 3 Drawing Sheets (51) Int. Cl.
*C01B 3/38* (2006.01)
*C07C 4/02* (2006.01)
*C07C 5/333* (2006.01)

(52) U.S. Cl.
CPC ............... *C01B 2203/0283* (2013.01); *C01B 2203/061* (2013.01)

(58) Field of Classification Search
CPC ......... C07C 1/04; C07C 1/12; C07C 29/1518; C07C 31/04; C07C 1/0425; C07C 2/04; C07C 2/82; C07C 4/04; B01J 8/001; B01J 8/0457; B01J 8/0492; B01J 8/0496
See application file for complete search history.

PROCESSES FOR IMPROVING THE EFFICIENCY OF HYDROCARBON PRODUCTION

CROSS-REFERENCE TO RELATED APPLICATIONS

This application is a National Stage Entry under 35 U.S.C. 071 of International Patent Application No. PCT/US2018/054954, filed Oct. 9, 2018, which claims priority to U.S. Provisional Patent Application Ser. No. 62/570,325 filed Oct. 10, 2017, both of which are incorporated by reference herein their entirety.

This application claims priority to U.S. Provisional Patent Application Ser. No. 62/570,325 filed Oct. 10, 2017, which is incorporated by reference herein its entirety.

BACKGROUND

Field

The present specification generally relates to processes and systems for converting feed carbon to desired products while minimizing the conversion of the feed carbon to carbon dioxide ($CO_2$). In particular, the present specification relates to processes that use a hybrid catalyst and recycled hydrogen ($H_2$) to achieve a high conversion of carbon contained in a synthesis gas feed stream, to desired products while minimizing the conversion of the feed carbon to $CO_2$.

Technical Background

For a number of industrial applications, a desirable starting material is a lower hydrocarbon—including, in particular, $C_2$ to $C_5$ olefins, and/or $C_2$ to $C_5$ paraffins that can then be converted to olefins—for use in or as starting materials to produce plastics, fuels, and various downstream chemicals. These $C_2$ to $C_5$ materials may be saturated or unsaturated and therefore may include ethane, ethylene, propane, propylene, butane, butylene, pentane, and/or pentylene. A variety of processes of producing these lower hydrocarbons has been developed, including petroleum cracking and various synthetic processes.

Synthetic processes for converting feed carbon to desired products, such as hydrocarbons, are known. Some of these synthetic processes begin with use of a hybrid catalyst. Different types of catalysts have also been explored, as well as different kinds of feed streams and proportions of feed stream components. However, many of these synthetic processes have low carbon conversion and much of the feed carbon does not get converted and exits the process in the same form as the feed carbon, or the feed carbon is converted to $CO_2$.

Accordingly, a need exists for processes that have a high conversion of feed carbon to desired products, such as, for example, $C_2$ to $C_5$ hydrocarbons.

SUMMARY

According to one embodiment, a process for converting a feed stream having carbon to $C_2$ to $C_5$ olefins, comprises: introducing a feed stream comprising methane and oxygen to a first reaction zone; reacting the methane and oxygen in the first reaction zone to form a first reaction zone product stream comprising a mixture of $C_2$ to $C_5$ alkanes; transporting the mixture of $C_2$ to $C_5$ alkanes to a second reaction zone; introducing a fresh stream of at least one of ethane and propane to the second reaction zone; converting the mixture of $C_2$ to $C_5$ alkanes to $C_2$ to $C_5$ olefins in the second reaction zone; producing one or more product streams in the second reaction zone, wherein a sum of the one or more product streams comprises $C_2$ to $C_5$ olefins; and producing a recycle stream comprising hydrogen in the second reaction zone, wherein the recycle stream is transported to the first reaction zone.

In one or more embodiments, the second reaction zone comprises a cracker, and a fresh stream of ethane is introduced into the cracker.

In some embodiments, the second reaction zone comprises a cracker and a propane dehydrogenation reactor, and a fresh stream of propane is introduced into the propane dehydrogenation reactor.

In still other embodiments, the second reaction zone comprises a cracker and a propane dehydrogenation reactor. A fresh stream of ethane is introduced into the cracker and a fresh stream of propane is introduced into the propane dehydrogenation reactor.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Reference will now be made in detail to embodiments of processes for converting a carbon-containing feed gas to a stream comprising $C_2$ to $C_5$ hydrocarbons, such as, for example a stream comprising $C_2$ to $C_5$ olefins, embodiments of which are illustrated in the accompanying drawings. Whenever possible, the same reference numerals will be used throughout the drawings to refer to the same or like parts. In one embodiment, a process for converting a feed stream comprising carbon to $C_2$ to $C_5$ olefins, comprises: introducing a feed stream comprising methane and oxygen to a first reaction zone; reacting the methane and oxygen in the first reaction zone to form a first reaction zone product stream comprising a mixture of $C_2$ to $C_5$ alkanes; transporting the mixture of $C_2$ to $C_5$ alkanes to a second reaction zone; introducing a fresh stream of at least one of ethane and propane to the second reaction zone; converting the mixture of $C_2$ to $C_5$ alkanes to $C_2$ to $C_5$ olefins in the second reaction zone; producing a second reaction zone product stream comprising $H_2$ and a mixture of $C_2$ to $C_5$ olefins; separating the second reaction zone product stream into a product stream comprising $C_2$ to $C_5$ olefins and recycle stream comprising $H_2$; and transporting the recycle stream to the first reaction zone.

Figure 1:
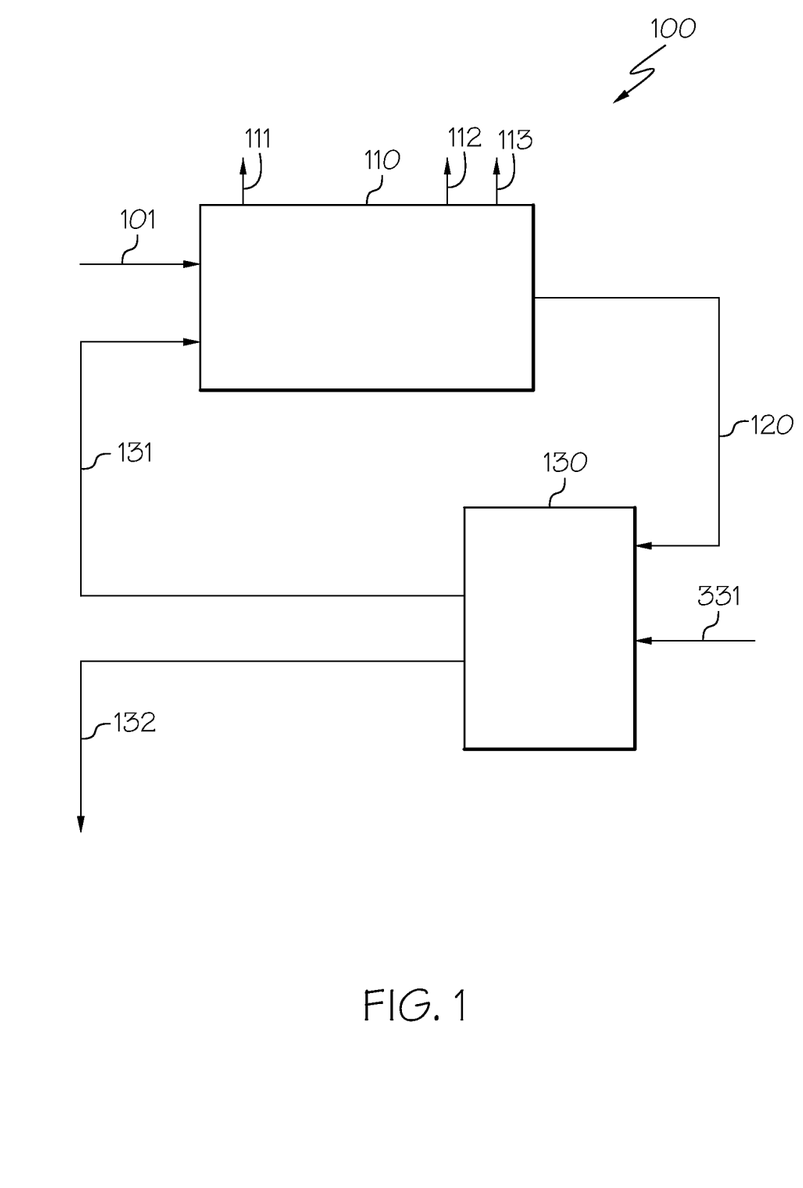
FIG. 1 schematically depicts a first embodiment of a system and process for converting a feed stream containing carbon to $C_2$ to $C_5$ olefins according to embodiments disclosed and described herein.

With reference now to FIG. 1, an embodiment of system for converting a feed stream containing carbon to $C_2$ to $C_5$ hydrocarbons is provided. It should be understood that the embodiment depicted in FIG. 1 is exemplary and does not limit the scope of this disclosure. As shown in the embodiment depicted in FIG. 1, a system 100 for converting a feed stream containing carbon to $C_2$ to $C_5$ hydrocarbons includes a first reaction zone 110, and a second reaction zone 130 that is fluidly connected to the first reaction zone 110.

A process, according to one or more embodiments, for converting a feed stream containing carbon to $C_2$ to $C_5$ hydrocarbons using the system 100 depicted in the embodiment of FIG. 1 will now be described. A feed stream 101 comprising methane ($CH_4$), oxygen ($O_2$), and, optionally, water is introduced into the first reaction zone 110. It should be understood that the feed stream 101 may contain carbon sources other than methane, such as ethane, propane, butane, and low levels of $CO_2$ according to various embodiments.

The first reaction zone 110, according to embodiments, may comprise a reformer (not shown) that uses water to convert the methane in the feed stream 101 to carbon monoxide (CO) and hydrogen in a conventional syngas generation process. For instance, according to one or more embodiments, the outlet of the reformer is at equilibrium for the following reactions: (1) $CH_4+H_2O \rightarrow CO+3H_2$; and (2) $CO+H_2O \rightarrow H_2+CO_2$. Additionally, unreacted methane and water will be present at the outlet of the reformer. Although the temperature at which the reformer is operated is not particularly limited so long as it can drive the above reactions, in one or more embodiments, the reformer is operated at an inlet temperature from greater than or equal to 400 degrees Celsius (° C.) to less than or equal to 450° C., such as from greater than or equal to 415° C. to less than or equal to 435° C., or about 425° C. Likewise, the pressure at which the reformer is operated is not particularly limited so long as it can drive the above reactions, in one or more embodiments, the reformer is operated at a pressure of greater than or equal to 38 bar (3.8 MPa) to less than or equal to 46 bar (4.6 MPa), such as from greater than or equal to 40 bar (4.0 MPa) to less than or equal to 44 bar (4.4 MPa), or about 42 bar (4.2 MPa). In embodiments, the feed into the reformer may comprise from greater than or equal to 30 wt % methane to less than or equal to 40 wt % methane, such as from greater than or equal to 33 wt % methane to less than or equal to 38 wt % methane, or about 36 wt % methane. Accordingly, in embodiments, the feed into the reformer may comprise from greater than or equal to 60 wt % water to less than or equal to 70 wt % water, such as from greater than or equal to 62 wt % water to less than or equal to 67 wt % water, or about 63 wt % water.

Once the methane and water are converted into carbon monoxide and hydrogen (i.e., syngas) as disclosed above, the outlet stream of the reformer is introduced into a partial oxidation (PDX) reactor (not shown). In embodiments, the following reactions occur in the PDX reactor: (3) $CH_4+0.5O_2 \rightarrow CO+2H_2$; and (4) $CH_4+2O_2 \rightarrow CO_2+2H_2O$. In these reactions, and according to embodiments, greater than or equal to 5 wt % to less than or equal to 15 wt % of the methane is converted to $CO_2$, such as greater than or equal to 7 wt % to less than or equal to 12 wt % of the methane is converted to $CO_2$, or about 10 wt % of the methane is converted to $CO_2$. Accordingly, in embodiments, greater than or equal to 85 wt % to less than or equal to 95 wt % of the methane is converted to CO, such as greater than or equal to 87 wt % to less than or equal to 92 wt % of the methane is converted to CO, or about 90 wt % of the methane is converted to CO. In embodiments, the outlet temperature of the PDX reactor may be from greater than or equal to 900° C. to less than or equal to 1100° C., such as from greater than or equal to 950° C. to less than or equal to 1050° C., or about 1000° C. Because the outlet temperature of the PDX reactor is higher than the reaction temperature of the reformer, heat from the PDX reactor may be directed to the reformer to improve the energy efficiency of the first reaction zone 110.

The outlet stream from the PDX reactor may then be introduced to a hybrid reactor where the outlet stream from the PDX reactor contacts a hybrid catalyst. The hybrid catalyst may, according to one or more embodiments, include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the methanol synthesis component may comprise one or more of the elements Cu, Zn, Cr, and Al, in any possible compositional combination and in either metallic or oxidic form. In embodiments, the solid microporous acid component is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type.

The use of hybrid catalysts to convert carbon-containing streams to desired products, such as, for example, $C_2$ to $C_5$ hydrocarbons, is known. In summary, hybrid catalysts closely couple sequential reactions on each of the two independent catalysts. In the first step, a stream, such as, for example, syngas, is converted into oxygenated hydrocarbons (mostly methanol and DME). In the second step, these oxygenates are converted into hydrocarbons (mostly short chain hydrocarbons, such as, for example $C_2$ to $C_5$ hydrocarbons). The continued withdrawal of oxygenates formed in the first step by the reactions of the second step ensure that there is no thermodynamic limit to achieve close to 100% (>99.9%) feed carbon conversion to hydrocarbons.

Surprisingly, it has been found that known solutions in the syngas-to-products field dealing with the formation of $CO_2$ are not desirable for the hybrid catalyst system. In more generic syngas-to-products processes, there are basically two options for dealing with the formation of $CO_2$; purging $CO_2$, or recycling $CO_2$ "to extinction" back to a syngas reformer section or over a catalytic reactor. The first option (purging) leads to a significant carbon yield loss and is only feasible when the amount of $CO_2$ is very low, which is not the case for the hybrid catalyst process. It has also been found that the second option (recycling $CO_2$) is not desirable for the hybrid process for at least two reasons: it leads to a large and expensive separation section to separate $CO_2$ from the desired product; and it negatively impacts the catalyst productivity.

In view of the above problems, there is presently no efficient way to deal with the loss of feed carbon to $CO_2$. To address these problems, embodiments of processes and systems disclosed herein recycle hydrogen from the downstream second reaction zone 130 to the first reaction zone 110 to further drive the conversion of carbon in the feed stream 101 to $C_2$ to $C_5$ hydrocarbons. It should be understood that the systems and processes for converting carbon-containing streams to $C_2$ to $C_5$ hydrocarbons disclosed herein are not required to use a hybrid catalyst to convert carbon-containing streams to $C_2$ to $C_5$ hydrocarbons. However, according to some embodiments, the systems and processes for converting carbon-containing streams to $C_2$ to $C_5$ hydrocarbons disclosed herein are particularly beneficial to processes using a hybrid catalyst.

The outlet stream from the PDX reactor is contacted with the hybrid catalyst under reaction conditions sufficient to form a first reaction zone product stream 120. The reaction conditions may comprise: a temperature ranging from greater than or equal to 300° C. to less than or equal to 450° C., such as from greater than or equal to 350° C. to less than or equal to 430° C., or from greater than or equal to 360° C. to less than or equal to 420° C.; and a pressure of at least 1 bar (100 kPa), such as at least 2 bar (200 kPa), or at least 3 bar (300 kPa). In other embodiments, the pressure may at least 15 bar (1500 kPa), at least 25 bar (2500 kPa), at least 30 bar (3000 kPa), at least 40 bar (4000 kPa), or at least 50 bar (5000 kPa). The processes that occur in the first reaction zone 110 produce CO, $CO_2$, $H_2$, $H_2O$, $CH_4$ and $C_2$ to $C_5$ hydrocarbons. In addition, inerts (such as, for example, nitrogen) that are present in the feed stream will exit the first reaction zone as a purge stream. In embodiments these components may be separated and removed from the first reaction zone in different streams. However, in embodiments, a light stream that comprises $H_2$, CO, $CO_2$, and $CH_4$ is recycled and reused in the first reaction zone 110, such as by transferring this light stream back to the reformer and the hybrid reactor. The systems and methods for separating these streams are known, and any suitable separation can be conducted. Conventional separators, such as acid gas removal processes for $CO_2$, and simple condensation for water removal, may be used. In embodiments, such as the embodiment depicted in FIG. 1, at least four streams exit the first reaction zone 110. A first exit stream 111 comprises, consists essentially of, or consists of $H_2O$. A second exit stream 112 is a purge stream that purges inert gases, such as, for example, nitrogen, from the first reaction zone. A third exit stream 113 comprises, consists essentially of, or consists of $CO_2$. The final stream that exits the first reaction zone 110 in the embodiment depicted in FIG. 1 is a first reaction zone product stream 120, which comprises $C_2$ to $C_5$ hydrocarbons. In one or more embodiments, the $C_2$ to $C_5$ hydrocarbons comprise, consist essentially of, or consist of $C_2$ to $C_5$ alkanes. It should be understood that, in embodiments, the first reaction zone product stream 120 may comprise $C_2$ to $C_5$ hydrocarbons other than $C_2$ to $C_5$ alkanes. In the embodiment depicted in FIG. 1, the first reaction zone product stream 120 is transferred to the second reaction zone 130.

It should be understood that according to various embodiments, the components of the first reaction zone, such as, for example, the reformer, the PDX reactor, and the reactor containing a hybrid catalyst, may be physically separate units or may be differentiated zones in a single, physical unit. Embodiments include various combinations of components of the first reaction zone being physically separated or combined in a single, physical unit. In addition, although specific reactions and processes for forming $C_2$ to $C_5$ hydrocarbons are disclosed above as being a part of the first reaction zone 110, it should be understood that other processes for forming $C_2$ to $C_5$ hydrocarbons may be used in the first reaction zone 110 in addition to, or in place of, the processes disclosed above.

In the embodiment depicted in FIG. 1, the second reaction zone 130 comprises a cracker. The first reaction zone product stream 120 enters the second reaction zone 130 where at least a portion of the $C_2$ to $C_5$ hydrocarbons—which comprise, consist essentially of, or consist of $C_2$ to $C_5$ alkanes—in the first reaction zone product stream 120 are converted to $C_2$ to $C_5$ olefins, such as, for example, ethylene ($C_2H_4$), propylene ($C_3H_6$), and butylene ($C_4H_8$). Additional components that may be produced in the second reaction zone comprise $H_2$, $CH_4$, pyrolysis gas (pygas) and other heavy hydrocarbons, such as, for example, nonaromatic hydrocarbons that comprise more than five carbon atoms. It should also be understood that, in embodiments, not all the $C_2$ to $C_5$ alkanes in the first reaction zone product stream 120 will be converted to $C_2$ to $C_5$ olefins, and will remain as $C_2$ to $C_5$ alkanes. These unconverted $C_2$ to $C_5$ alkanes will exit the cracker with the other components, but the $C_2$ to $C_5$ alkanes do not exit the second reaction zone 130 and can be recycled back to the cracker.

According to embodiments, a fresh stream of ethane 331 may be introduced into the second reaction zone 130 in addition to first reaction zone product stream 120. The first reaction zone product stream 120 and the ethane in the fresh stream of ethane 331 may be converted into the second reaction zone product stream 132. The addition of the fresh stream of ethane 331 provides, upon conversion in second reaction zone 130, additional hydrogen that may be recycled back to the first reaction zone 110 as described in more detail below. In embodiments, any amount of ethane may be introduced into the second reaction zone 130. However, in various embodiments, the amount of the fresh stream of ethane 331 in the total feed to the second reaction zone 130 (i.e., the first reaction zone product stream 120 plus the fresh stream of ethane 331) comprises from greater than or equal to 5 wt % to less than or equal to 40 wt %, such as from greater than or equal to 10 wt % to less than or equal to 35 wt %, or about 30 wt %. If too little fresh ethane is introduced into the second reaction zone 130 via the fresh ethane stream 331, there will not be a sufficient amount of $H_2$ recycled back to the first reaction zone 110 to provide a desired reduction of $CO_2$ produced in the first reaction zone 110. However, if too much fresh ethane is introduced into the second reaction zone via the fresh ethane stream 331, part of the $H_2$ exiting the second reaction zone in the recycle stream 131 will need to be purged as fuel to prevent the buildup of $H_2$, which creates an inefficiency in the conversion process. It should be understood that any conventional steam cracker may be used in the second reaction zone 130 so long as it is capable of converting the $C_2$ to $C_5$ hydrocarbons in the first reaction zone product stream 120—which comprises, consists essentially of, or consists of $C_2$ to $C_5$ alkanes—combined with a fresh stream of ethane 331, to a second reaction zone product stream 132 that comprises $C_2$ to $C_5$ olefins.

As discussed above, multiple components may exit the cracker, such as, for example, $C_2$ to $C_5$ alkanes, $C_2$ to $C_5$ olefins, $H_2$, $CH_4$, pyrolysis gas (pygas) and other heavy hydrocarbons. Thus, within the second reaction zone these various products may be separated and recycled, collected, or discarded. It should be understood that conventional separators, such as, for example, cryogenic separators, may be used to separate the components that exit the cracker in the second reaction zone 130. For instance, in the second reaction zone 130 at least three separations may occur: (1) $C_2$ to $C_5$ olefins may be separated from the components exiting the cracker; (2) $C_2$ to $C_5$ alkanes may be separated from the components exiting the cracker, and (3) $H_2$ and, optionally, $CH_4$ may be separated from the components that exit the cracker. Other components that comprise more than 5 carbon atoms may, in embodiments, be discarded from the second reaction zone 130 and used in other systems as desired.

Although not shown in FIG. 1, the $C_2$ to $C_5$ alkanes that exit the cracker may be recycled back to the cracker where they may be combined with the $C_2$ to $C_5$ alkanes that enter the cracker from the first reaction zone product stream 120 and processed into $C_2$ to $C_5$ olefins. One stream that exits the second reaction zone 130 is a recycle stream 131 that comprises, consists essentially of, or consists of $H_2$. In some embodiments, the recycle stream 131 comprises, consists essentially of, or consists of $H_2$ and $CH_4$. Another stream that exits the second reaction zone 130 is a product stream 132 that comprises, consists essentially of, or consists of $C_2$ to $C_5$ hydrocarbons—which comprise, consist essentially of, or consists of $C_2$ to $C_5$ olefins. The product stream 132 is collected and used in various other processes to make end products. The recycle stream 131 is transferred from the second reaction zone 130 to the first reaction zone 110. Thus, in some embodiments, $H_2$ is recycled from second reaction zone 130 to the first reaction zone 110. In other embodiments, $H_2$ and $CH_4$ are recycled from the second reaction zone 130 to the first reaction zone 110. It should be understood that the amount of $H_2$ recycled back to the first reaction zone 110 in recycle stream 131 is determined by the amount of ethane added to the second reaction zone 130.

By introducing a fresh ethane stream 331 into the second reaction zone 130 and by recycling $H_2$ to the first reaction zone 110, certain mass balances may be achieved in the streams exiting the first reaction zone (i.e., the first exit stream 111, the second exit stream 112, the third exit stream 113, and the first reaction zone product stream 120) and in the streams exiting the second reaction zone (i.e., the recycle stream 131 and the product stream 132). The mass flow of the components present in the streams exiting the first reaction zone, which is based on 1 pound (lb.) of ethylene produced, includes from greater than or equal to 0.085 lbs. to less than or equal to 0.095 lbs. pentane ($C_5H_{12}$), such as about 0.088 lbs. $C_5H_{12}$; from greater than or equal to 0.170 lbs. to less than or equal to 0.185 lbs. butane ($C_4H_{10}$), such as about 0.177 lbs. $C_4H_{10}$; from greater than or equal to 0.500 lbs. to less than or equal to 0.650 lbs. propane ($C_3H_8$), such as about 0.571 lbs. $C_3H_8$; from greater than or equal to 0.300 lbs. to less than or equal to 0.400 lbs. ethane ($C_2H_6$), such as about 0.342 lbs. $C_2H_6$; from greater than or equal to 1.200 lbs. to less than or equal to 1.500 lbs. water ($H_2O$), such as about 1.370 lbs. $H_2O$; and less than or equal to 0.010 lbs. $CO_2$, such as less than 0.005 lbs. $CO_2$, less than 0.001 lbs. $CO_2$, or even no $CO_2$.

In one or more embodiments, the mass flow of the components in the streams exiting the second reaction zone, which is based on 1 lb. of ethylene produced, includes from greater than or equal to 0.0500 lbs. to less than or equal to 0.0700 lbs. $H_2$, such as about 0.0598 lbs. $H_2$; from greater than or equal to 0.1500 lbs. to less than or equal to 0.3500 lbs. $CH_4$, such as about 0.2626 lbs. $CH_4$; about 1.0000 lbs. $C_2H_4$; from greater than or equal to 0.0500 lbs. to less than or equal to 0.2500 lbs. $C_3H_6$, such as about 0.1598 lbs. $C_3H_6$; from greater than or equal to 0.0750 lbs. to less than or equal to 0.0950 lbs. $C_4H_8$, such as about 0.0854 lbs. $C_4H_8$; from greater than or equal to 0.0700 lbs. to less than or equal to 0.0900 lbs. pygas, such as about 0.0813 lbs. pygas; and from greater than or equal to 0.0110 lbs. to less than or equal to 0.0130 lbs. of other heavy hydrocarbons, such as about 0.0124 lbs. other heavy hydrocarbons.

Figure 2A:
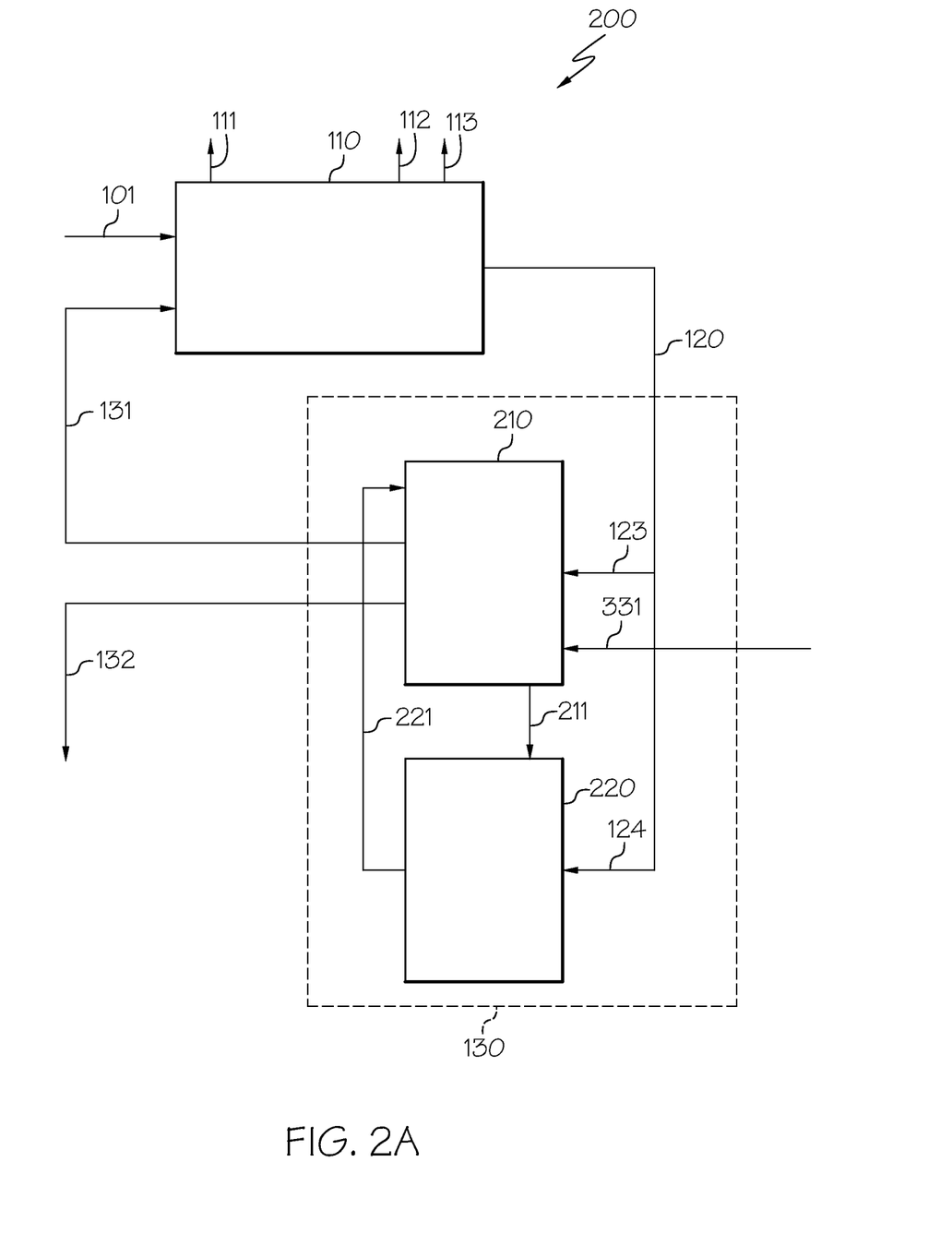
FIG. 2A schematically depicts a second embodiment of a system and process for converting a feed stream containing carbon to $C_2$ to $C_5$ olefins according to embodiments disclosed and described herein.

With reference to the embodiment depicted in FIG. 2A, an embodiment of system for converting a feed stream containing carbon to $C_2$ to $C_5$ hydrocarbons is provided. It should be understood that the embodiment depicted in FIG. 2A is exemplary and does not limit the scope of this disclosure. As shown in the embodiment depicted in FIG. 2A, a system 200 for converting a feed stream containing carbon to $C_2$ to $C_5$ hydrocarbons includes a first reaction zone 110, and a second reaction zone 130—which comprises a cracker 210 and a propane dehydrogenation (PDH) reactor 220—that is fluidly connected to the first reaction zone 110.

A process, according to one or more embodiments, for converting a feed stream containing carbon to $C_2$ to $C_5$ hydrocarbons using the system 200 depicted in the embodiment of FIG. 2A will now be described. A feed stream 101 comprising methane ($CH_4$), oxygen ($O_2$), and, optionally, water is introduced into the first reaction zone 110. It should be understood that the feed stream 101 may contain carbon sources other than methane, such as ethane, propane, butane, and low levels of $CO_2$ according to various embodiments.

The first reaction zone 110, according to embodiments, may comprise a reformer (not shown) that uses water to convert the methane in the feed stream 101 to CO and $H_2$ in a conventional syngas generation process. The reactions and reaction conditions of the reformer are provided above with reference to the embodiment depicted in FIG. 1.

Once the methane and water are converted into carbon monoxide and hydrogen (i.e., syngas), the outlet stream of the reformer is introduced into a PDX reactor. The reactions and reaction conditions of the PDX reactor are provided above with reference to the embodiment depicted in FIG. 1. Because the outlet temperature of the PDX reactor is higher than the reaction temperature of the reformer, heat from the PDX reactor may be directed to the reformer to improve the energy efficiency of the first reaction zone 110.

The outlet stream from the PDX reactor may then be introduced to a hybrid reactor where the outlet stream from the PDX reactor contacts a hybrid catalyst. The hybrid catalyst may, according to one or more embodiments, include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the methanol synthesis component may comprise one or more of the elements Cu, Zn, Cr, and Al, in any possible compositional combination and in either metallic or oxidic form. In embodiments, the solid microporous acid component is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type.

The processes that occur in the first reaction zone 110 produce CO, $CO_2$, $H_2$, $H_2O$, $CH_4$, and $C_2$ to $C_5$ hydrocarbons. In addition, inerts (such as, for example, nitrogen) that are present in the feed stream will exit the first reaction zone as a purge stream. In embodiments these components may be separated and removed from the first reaction zone in different streams. However, in embodiments, a light stream that comprises $H_2$, CO, $CO_2$, and $CH_4$ is recycled and reused in the first reaction zone 110, such as by transferring this light stream back to the reformer and the hybrid reactor. The systems and methods for separating these streams are known, and any suitable separation can be conducted. Conventional separators, such as acid gas removal processes for $CO_2$, and simple condensation for water removal, may be used. In embodiments, such as the embodiment depicted in FIG. 2A, at least four streams exit the first reaction zone 110. A first exit stream 111 comprises, consists essentially of, or consists of $H_2O$. A second exit stream 112 is a purge stream that purges inert gases, such as, for example, nitrogen, from the first reaction zone. A third exit stream 113 comprises, consists essentially of, or consists of $CO_2$. The final stream that exits the first reaction zone 110 in the embodiment depicted in FIG. 2A is a first reaction zone product stream 120, which comprises $C_2$ to $C_5$ hydrocarbons. In one or more embodiments, the $C_2$ to $C_5$ hydrocarbons comprise, consist essentially of, or consist of $C_2$ to $C_5$ alkanes. It should be understood that, in embodiments, the first reaction zone product stream 120 may comprise $C_2$ to $C_5$ hydrocarbons other than $C_2$ to $C_5$ alkanes. In the embodiment depicted in FIG. 2A, the first reaction zone product stream 120 is transferred to the second reaction zone 130.

It should be understood that according to various embodiments, the components of the first reaction zone 110, such as, for example, the reformer, the PDX reactor, and the reactor containing a hybrid catalyst, may be physically separate units or may be differentiated zones in a single, physical unit. Embodiments include various combinations of components of the first reaction zone 110 being physically separated or combined in a single, physical unit. In addition, although specific reactions and processes for forming $C_2$ to $C_5$ hydrocarbons are disclosed above as being a part of the first reaction zone 110, it should be understood that other processes for forming $C_2$ to $C_5$ hydrocarbons may be used in the first reaction zone 110 in addition to, or in place of, the processes disclosed above.

In the embodiment depicted in FIG. 2A, the second reaction zone 130 comprises a cracker 210 and a PDH reactor 220. The first reaction zone product stream 120 enters the second reaction zone 130. In the embodiment depicted in FIG. 2A, the first reaction zone product stream 120 is separated by a separator (not shown) in the second reaction zone 130 into a first stream 123 comprising $C_2$, $C_4$, and $C_5$ hydrocarbons and a second stream 124 comprising $C_3$ hydrocarbons. The first stream 123 is introduced into the cracker 210 and the second stream 124 is introduced into the PDH reactor 220. It should be understood that any conventional separator may be used to separate the first reaction zone product stream 120 into the first stream 123 and the second stream 124.

In the cracker 210 $C_2$, $C_4$, and $C_5$ alkanes, which are present in the first stream 123, are reacted to form $C_2$, $C_3$, $C_4$, and $C_5$ olefins. It should be understood that any conventional cracker 210—such as those available for license from Technip, CB&I or other technology providers, also referred to a steam crackers, or cracking furnaces—may be used in the second reaction zone 130 so long as it is capable of converting the $C_2$, $C_4$, and $C_5$ hydrocarbons in the first stream 123—which comprises, consists essentially of, or consists of $C_2$, $C_4$, and $C_5$ alkanes—to a stream that comprises $C_2$, $C_3$, $C_4$, and $C_5$ olefins. Additional components that may be produced in the cracker 210 comprise $H_2$, $CH_4$, pyrolysis gas (pygas) and other heavy hydrocarbons, such as, for example, nonaromatic hydrocarbons that comprise more than five carbon atoms. It should also be understood that, in embodiments, not all the $C_2$, $C_4$, and $C_5$ alkanes in the first stream 123 will be converted to $C_2$, $C_3$, $C_4$, and $C_5$ olefins. Thus, unconverted $C_2$, $C_4$, and $C_5$ alkanes will exit the cracker with the other components. Although not shown in FIG. 2A, these unconverted $C_2$, $C_4$, and $C_5$ alkanes may be separated from the cracker output using conventional separation techniques and equipment (not shown) and recycled back to the cracker, such as, for example, by combining them with the $C_2$, $C_4$, and $C_5$ alkanes in the first stream 123. In addition, $H_2$ and $CH_4$ present in the cracker output may be separated from other components of the cracker output using conventional separation techniques and equipment (not shown) and recycled back to the first reaction zone 110 in recycle stream 131. The $C_2$, $C_3$, $C_4$, and $C_5$ olefins produced in the cracker 210, may exit the second reaction zone 130 as a product stream 132 where it may be collected for use as a starting material in other processes. Other components produced in the cracker 210 may be separated using conventional techniques and equipment (not shown) as desired and discarded from the system 200. Additionally, any propane may be separated from the streams exiting the cracker 210 and sent to the PDH reactor 220 in a propane-comprising stream 211.

According to embodiments, a fresh stream of ethane 331 may be introduced into the cracker 210 in addition to the first stream 123. The $C_2$, $C_4$, and $C_5$ alkanes in the first stream 123 and the ethane in the fresh stream of ethane 331 may be converted into $C_2$, $C_3$, $C_4$, and $C_5$ olefins. The addition of the fresh stream of ethane 331 provides, upon conversion in cracker 210, additional $H_2$ that may be recycled back to the first reaction zone 110, as described in more detail below. In embodiments, any amount of ethane may be introduced into the second reaction zone 130. However, in various embodiments, the amount of the fresh stream of ethane 331 in the total feed to the cracker 210 (i.e., the first stream 123 plus the fresh ethane stream 331) comprises from greater than or equal to 5 wt % to less than or equal to 30 wt %, such as from greater than or equal to 10 wt % to less than or equal to 25 wt %, or about 17.5 wt %. If too little fresh ethane is introduce into the cracker 210 via the fresh ethane stream 331, there will not be a sufficient amount of $H_2$ recycled back to the first reaction zone 110 to provide a desired reduction of $CO_2$ produced in the first reaction zone 110. However, if too much fresh ethane is introduced into the cracker 210 via the fresh ethane stream 331, part of the $H_2$ exiting the cracker 210 will need to be purged as fuel to prevent the buildup of $H_2$, which creates an inefficiency in the conversion process. It should be understood that any conventional cracker 210—such as those available for license from Technip, CB&I or other technology providers, also referred to a steam crackers, or cracking furnaces—may be used in the second reaction zone 130 so long as it is capable of converting the $C_2$, $C_4$, and $C_5$ hydrocarbons in the first stream 123—which comprises, consists essentially of, or consists of $C_2$, $C_4$, and $C_5$ alkanes—combined with a fresh stream of ethane 331, to a stream that comprises $C_2$, $C_3$, $C_4$, and $C_5$ olefins.

In the PDH reactor 220, $C_3H_8$, which is present in the second stream 124, is converted to $C_3H_6$. It should be understood that any conventional PDH reactor 220—such as, for example, UOP's Oleflex, CB&I Catofin, and Uhde STAR—may be used in the second reaction zone 130 so long as it is capable of converting the $C_3H_8$ in the second stream 124 to $C_3H_6$. It should be understood that, in embodiments, not all of the $C_3H_8$ that enters the PDH reactor 220 will be converted to $C_3H_6$. Accordingly, the PDH reactor stream 221 that exits the PDH reactor 220 may comprise $C_3H_6$, $C_3H_8$, and one or more of $H_2$, $CH_4$, unreacted alkanes, and hydrocarbons comprising more than 5 carbons.

The PDH reactor stream 221 is sent from the PDH reactor 220 to a separation section of the cracker 210. Although not depicted in FIG. 2A, in embodiments, the cracker 210 includes a separation section that separates the various components formed in the cracker as well as the various components present in the PDH reactor stream 221. In the separation section of the cracker 210, the $C_3H_6$ in the PDH reactor stream 221 will be separated from the PDH reactor stream 221 where it may, in embodiments, be combined with the product stream 132 that exits the second reaction zone 130 and is collected for further use. Likewise, in embodiments, $H_2$ and, optionally, $CH_4$ that are present in the PDH reactor stream 221 may be separated from the PDH reactor stream 221 in the separation section of the cracker 210 and combined with recycle stream 131, where it exits the second reaction zone 130 and is recycled by being sent to the first reaction zone 110. Unreacted alkanes in the PDH reactor stream 221 may, in one or more embodiments, be separated from the PDH reactor stream 221 in the separation section of the cracker 210 where the unreacted alkanes can be further processed by the cracker 210 and converted into $C_2$ to $C_5$ olefins that can exit the second reaction zone in product stream 132. However, any propane present in the PDH reactor stream 221 will, in embodiments, be returned to the PDH reactor 220 in a propane-comprising stream 211, where the propane may be processed by the PDH reactor and converted to $C_3H_6$. Any hydrocarbons comprising more than 5 carbons present in the PDH reactor stream 221 may, in some embodiments, be separated from the PDH reactor stream 221 in the separation section of the cracker 210 and discarded from the second reaction zone 130 in a discard stream (not shown).

It should be understood that according to various embodiments, the components of the second reaction zone 130, such as, for example, the cracker 210 (including the separation section of the cracker), and the PDH reactor 220, may be physically separate units or may be differentiated zones in a single, physical unit. Embodiments include various combinations of components of the second reaction zone 130 being physically separated or combined in a single, physical unit.

By introducing a fresh ethane stream 331 into the second reaction zone 130 and by recycling $H_2$ to the first reaction zone 110, certain mass balances may be achieved in the streams exiting the first reaction zone (i.e., the first exit stream 111, the second exit stream 112, the third exit stream 113, and the first reaction zone product stream 120) and in the streams exiting the second reaction zone (i.e., the recycle stream 131 and the product stream 132. It should be understood that where more than one product stream exits the second reaction zone 130, the combination of all the product streams exiting the second reaction zone 130 may be referred to as "a sum of the one or more product streams". In one or more embodiments, the mass flow of the components present in the streams exiting the first reaction zone, which is based on 1 lb. of ethylene produced, includes from greater than or equal to 0.050 lbs. to less than or equal to 0.250 lbs. $C_5H_{12}$, such as about 0.152 lbs. $C_5H_{12}$; from greater than or equal to 0.200 lbs. to less than or equal to 0.400 lbs. $C_4H_{10}$, such as about 0.304 lbs. $C_4H_{10}$; from greater than or equal to 0.850 lbs. to less than or equal to 1.050 lbs. $C_3H_8$, such as about 0.984 lbs. $C_3H_8$; from greater than or equal to 0.450 lbs. to less than or equal to 0.650 lbs. $C_2H_6$, such as about 0.588 lbs. $C_2H_6$; from greater than or equal to 2.200 lbs. to less than or equal to 2.500 lbs. $H_2O$, such as about 2.360 lbs. $H_2O$; and less than or equal to 0.010 lbs. $CO_2$, such as less than 0.005 lbs. $CO_2$, less than 0.001 lbs. $CO_2$, or even no $CO_2$.

In one or more embodiments, the mass flow of the components present in the streams exiting the second reaction zone, which is based on 1 lb. of ethylene produced, includes from greater than or equal to 0.0900 lbs. to less than or equal to 0.1100 lbs. $H_2$, such as about 0.1036 lbs. $H_2$; from greater than or equal to 0.1900 lbs. to less than or equal to 0.2300 lbs. $CH_4$, such as about 0.2106 lbs. $CH_4$; about 1.0000 lbs. $C_2H_4$; from greater than or equal to 0.8000 lbs. to less than or equal to 1.0000 lbs. $C_3H_6$, such as about 0.9212 lbs. $C_3H_6$; from greater than or equal to 0.0900 lbs. to less than or equal to 0.1100 lbs. $C_4H_8$, such as about 0.0998 lbs. $C_4H_8$; from greater than or equal to 0.0700 lbs. to less than or equal to 0.0900 lbs. pygas, such as about 0.0863 lbs. pygas; and from greater than or equal to 0.0120 lbs. to less than or equal to 0.0150 lbs. of other heavy hydrocarbons, such as about 0.0139 lbs. other heavy hydrocarbons.

Figure 2B:
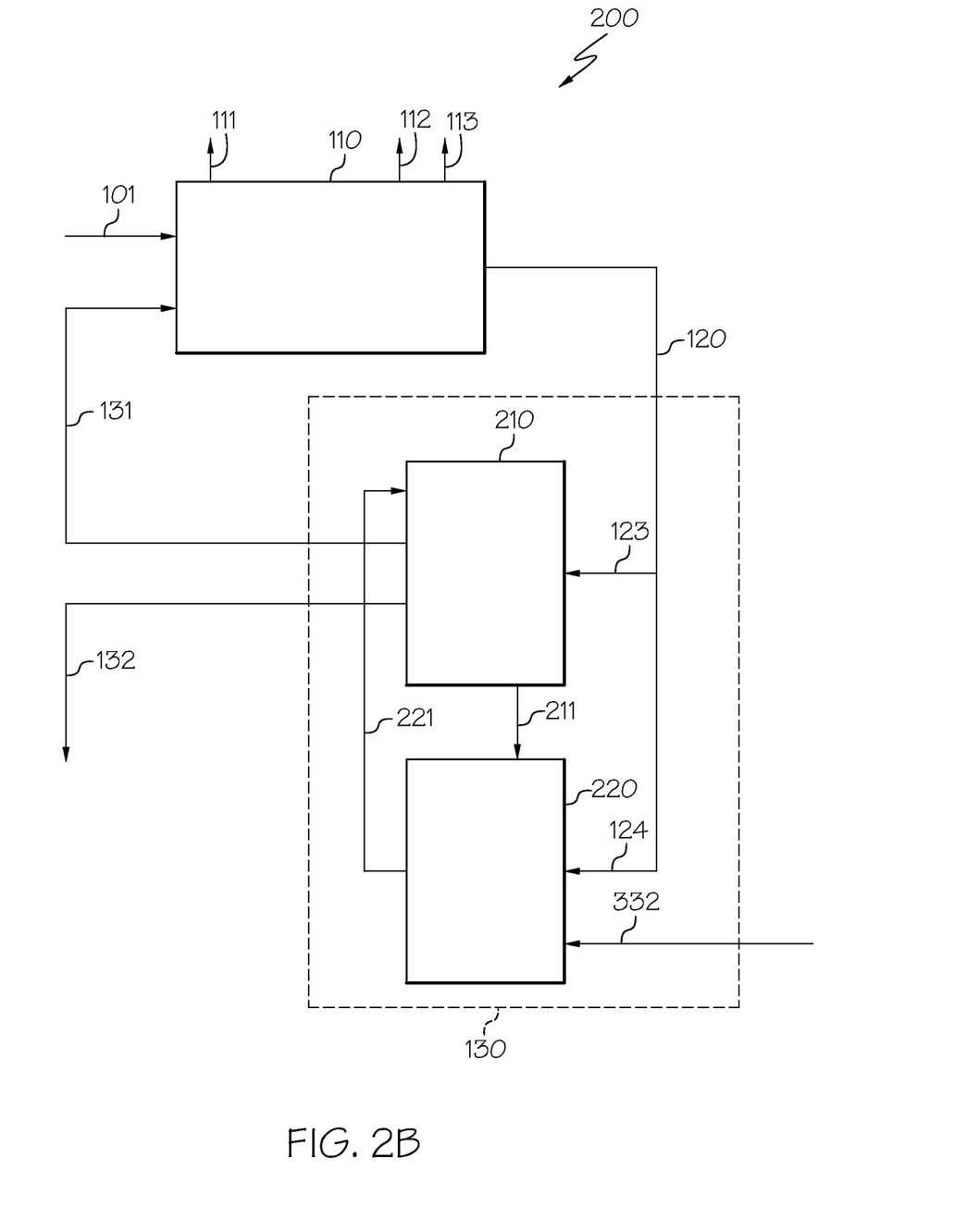
FIG. 2B schematically depicts a third embodiment of a system and process for converting a feed stream containing carbon to $C_2$ to $C_5$ olefins according to embodiments disclosed and described herein.

With reference to the embodiment depicted in FIG. 2B, an embodiment of system for converting a feed stream containing carbon to $C_2$ to $C_5$ hydrocarbons is provided. It should be understood that the embodiment depicted in FIG. 2B is exemplary and does not limit the scope of this disclosure. As shown in the embodiment depicted in FIG. 2B, a system 200 for converting a feed stream containing carbon to $C_2$ to $C_5$ hydrocarbons includes a first reaction zone 110, and a second reaction zone 130—which comprises a cracker 210 and a PDH reactor 220—that is fluidly connected to the first reaction zone 110.

A process, according to one or more embodiments, for converting a feed stream containing carbon to $C_2$ to $C_5$ hydrocarbons using the system 200 depicted in the embodiment of FIG. 2B will now be described. A feed stream 101 comprising methane ($CH_4$), oxygen ($O_2$), and, optionally, water is introduced into the first reaction zone 110. It should be understood that the feed stream 101 may contain carbon sources other than methane, such as ethane, propane, butane, and low levels of $CO_2$ according to various embodiments.

The first reaction zone 110, according to embodiments, may comprise a reformer (not shown) that uses water to convert the methane in the feed stream 101 to CO and $H_2$ in a conventional syngas generation process. The reactions and reaction conditions of the reformer are provided above with reference to the embodiment depicted in FIG. 1.

Once the methane and water are converted into carbon monoxide and hydrogen (i.e., syngas), the outlet stream of the reformer is introduced into a PDX reactor (not shown). The reactions and reaction conditions of the PDX reactor are provided above with reference to the embodiment depicted in FIG. 1. Because the outlet temperature of the PDX reactor is higher than the reaction temperature of the reformer, heat from the PDX reactor may be directed to the reformer to improve the energy efficiency of the first reaction zone 110.

The outlet stream from the PDX reactor may then be introduced to a hybrid reactor where the outlet stream from the PDX reactor contacts a hybrid catalyst. The hybrid catalyst may, according to one or more embodiments, include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the methanol synthesis component may comprise one or more of the elements Cu, Zn, Cr, and Al, in any possible compositional combination and in either metallic or oxidic form. In embodiments, the solid microporous acid component is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type.

The processes that occur in the first reaction zone 110 produce CO, $CO_2$, $H_2$, $H_2O$, $CH_4$, and $C_2$ to $C_5$ hydrocarbons. In addition, inerts (such as, for example, nitrogen) that are present in the feed stream will exit the first reaction zone as a purge stream. In embodiments these components may be separated and removed from the first reaction zone in different streams. However, in embodiments, a light stream that comprises $H_2$, CO, $CO_2$, and $CH_4$ is recycled and reused in reaction zone 110, such as by transferring this light stream back to the reformer and the hybrid reactor. The systems and methods for separating these streams are known, and any suitable separation can be conducted. Conventional separators, such as acid gas removal processes for $CO_2$, and simple condensation for water removal, may be used. In embodiments, such as the embodiment depicted in FIG. 2B, at least four streams exit the first reaction zone 110. A first exit stream 111 comprises, consists essentially of, or consists of $H_2O$. A second exit stream 112 is a purge stream that purges inert gases, such as, for example, nitrogen, from the first reaction zone. A third exit stream 113 comprises, consists essentially of, or consists of $CO_2$. The final stream that exits the first reaction zone 110 in the embodiment depicted in FIG. 2B is a first reaction zone product stream 120, which comprises $C_2$ to $C_5$ hydrocarbons. In one or more embodiments, the $C_2$ to $C_5$ hydrocarbons comprise, consist essentially of, or consist of $C_2$ to $C_5$ alkanes. It should be understood that, in embodiments, the first reaction zone product stream 120 may comprise $C_2$ to $C_5$ hydrocarbons other than $C_2$ to $C_5$ alkanes. In the embodiment depicted in FIG. 2B, the first reaction zone product stream 120 is transferred to the second reaction zone 130.

It should be understood that according to various embodiments, the components of the first reaction zone, such as, for example, the reformer, the PDX reactor, and the reactor containing a hybrid catalyst, may be physically separate units or may be differentiated zones in a single, physical unit. Embodiments include various combinations of components of the first reaction zone being physically separated or combined in a single, physical unit. In addition, although specific reactions and processes for forming $C_2$ to $C_5$ hydrocarbons are disclosed above as being a part of the first reaction zone 110, it should be understood that other processes for forming $C_2$ to $C_5$ hydrocarbons may be used in the first reaction zone 110 in addition to, or in place of, the processes disclosed above.

In the embodiment depicted in FIG. 2B, the second reaction zone 130 comprises a cracker 210 and a PDH reactor 220. The first reaction zone product stream 120 enters the second reaction zone 130. In the embodiment depicted in FIG. 2B, the first reaction zone product stream 120 is separated by a separator (not shown) in the second reaction zone 130 into a first stream 123 comprising $C_2$, $C_4$, and $C_5$ hydrocarbons and a second stream 124 comprising $C_3$ hydrocarbons. The first stream 123 is introduced into the cracker 210 and the second stream 124 is introduced into the PDH reactor 220. It should be understood that any conventional separator may be used to separate the first reaction zone product stream 120 into the first stream 123 and the second stream 124.

In the cracker 210 $C_2$, $C_4$, and $C_5$ alkanes, which are present in the first stream 123, are reacted to form $C_2$, $C_3$, $C_4$, and $C_5$ olefins. It should be understood that any conventional cracker 210—such as those available for license from Technip, CB&I or other technology providers, also referred to a steam crackers, or cracking furnaces—may be used in the second reaction zone 130 so long as it is capable of converting the $C_2$, $C_4$, and $C_5$ hydrocarbons in the first stream 123—which comprises, consists essentially of, or consists of $C_2$, $C_4$, and $C_5$ alkanes—to a stream that comprises $C_2$, $C_3$, $C_4$, and $C_5$ olefins. Additional components that may be produced in the cracker 210 comprise $H_2$, $CH_4$, pyrolysis gas (pygas) and other heavy hydrocarbons, such as, for example, nonaromatic hydrocarbons that comprise more than five carbon atoms. It should also be understood that, in embodiments, not all the $C_2$, $C_4$, and $C_5$ alkanes in the first stream 123 will be converted to $C_2$, $C_3$, $C_4$, and $C_5$ olefins. Thus, unconverted $C_2$, $C_4$, and $C_5$ alkanes will exit the cracker with the other components. Although not shown in FIG. 2B, these unconverted $C_2$, $C_4$, and $C_5$ alkanes may be separated from the cracker output using conventional separation techniques and equipment (not shown) and recycled back to the cracker, such as, for example, by combining them with the $C_2$, $C_4$, and $C_5$ alkanes in the first stream 123. In addition, $H_2$ and $CH_4$ present in the cracker output may be separated from other components of the cracker output using conventional separation techniques and equipment (not shown) and recycled back to the first reaction zone 110 in recycle stream 131. The $C_2$, $C_3$, $C_4$, and $C_5$ olefins produced in the cracker 210, may exit the second reaction zone 130 as a product stream 132 where it may be collected for use as a starting material in other processes. Other components produced in the cracker 210 may be separated using conventional techniques and equipment (not shown) as desired and discarded from the system 200. Additionally, any propane may be separated from the streams exiting the cracker 210 and sent to the PDH reactor 220 in a propane-comprising stream 211.

In the PDH reactor 220, $C_3H_8$, which is present in the second stream 124, is converted to $C_3H_6$. According to embodiments, a fresh stream of propane 332 may be introduced into the PDH reactor 220 in addition to the second stream 124. The $C_3H_8$ in the second stream 124 and the propane in the fresh stream of propane 332 may be converted into $C_3H_6$. The addition of the fresh stream of propane 332 provides, upon conversion in PDH reactor 220, additional hydrogen that may be recycled back to the first reaction zone 110 as described in more detail below. In embodiments, any amount of propane may be introduced into the second reaction zone 130. However, in various embodiments, the amount of the fresh stream of propane 332 in the total feed to the PDH reactor 220 (i.e., the second stream 124 plus the fresh propane stream 332) comprises from greater than or equal to 5 wt % to less than or equal to 30 wt %, such as from greater than or equal to 10 wt % to less than or equal to 25 wt %, or about 22 wt %. If too little fresh propane is introduce into the PDH reactor 220 via the fresh propane stream 332, there will not be a sufficient amount of $H_2$ recycled back to the first reaction zone 110 to provide a desired reduction of $CO_2$ produced in the first reaction zone 110. However, if too much fresh propane is introduced into the PDH reactor 220 via the fresh propane stream 332, part of the $H_2$ exiting the PDH reactor 220 will need to be purged as fuel to prevent the buildup of $H_2$, which creates an inefficiency in the conversion process. It should be understood that any conventional PDH reactor 220—such as, for example, UOP's Oleflex, CB&I Catofin, and Uhde STAR—may be used in the second reaction zone 130 so long as it is capable of converting the $C_3H_8$ in the second stream 124, combined with a fresh stream of propane 332, to $C_3H_6$. It should be understood that, in embodiments, not all of the $C_3H_8$ that enters the PDH reactor 220 will be converted to $C_3H_6$. Accordingly, the PDH reactor stream 221 that exits the PDH reactor 220 may comprise $C_3H_6$, $C_3H_8$, and one or more of $H_2$, $CH_4$, unreacted alkanes, and hydrocarbons comprising more than 5 carbons.

The PDH reactor stream 221 is sent from the PDH reactor 220 to a separation section of the cracker 210. Although not depicted in FIG. 2B, in embodiments, the cracker 210 includes a separation section that separates the various components formed in the cracker as well as the various components present in the PDH reactor stream 221. In the separation section of the cracker 210, the $C_3H_6$ in the PDH reactor stream 221 will be separated from the PDH reactor stream 221 where it may, in embodiments, be combined with the product stream 132 that exits the second reaction zone 130 and is collected for further use. Likewise, in embodiments, $H_2$ and, optionally, $CH_4$ that are present in the PDH reactor stream 221 may be separated from the PDH reactor stream 221 in the separation section of the cracker 210 and combined with recycle stream 131, where it exits the second reaction zone 130 and is recycled by being sent to the first reaction zone 110. Unreacted alkanes in the PDH reactor stream 221 may, in one or more embodiments, be separated from the PDH reactor stream 221 in the separation section of the cracker 210 where the unreacted alkanes can be further processed by the cracker 210 and converted into $C_2$ to $C_5$ olefins that can exit the second reaction zone in product stream 132. However, any propane present in the PDH reactor stream 221 will, in embodiments, be returned to the PDH reactor 220 in a propane-comprising stream 211, where the propane may be processed by the PDH reactor and converted to $C_3H_6$. Any hydrocarbons comprising more than 5 carbons present in the PDH reactor stream 221 may, in some embodiments, be separated from the PDH reactor stream 221 in the separation section of the cracker 210 and discarded from the second reaction zone 130 in a discard stream (not shown).

It should be understood that according to various embodiments, the components of the second reaction zone 130, such as, for example, the cracker 210 (including the separation section), and the PDH reactor 220, may be physically separate units or may be differentiated zones in a single, physical unit. Embodiments include various combinations of components of the second reaction zone 130 being physically separated or combined in a single, physical unit.

By introducing a fresh propane stream 332 into the second reaction zone 130 and by recycling $H_2$ to the first reaction zone 110, certain mass balances may be achieved in the streams exiting the first reaction zone (i.e., the first exit stream 111, the second exit stream 112, the third exit stream 113, and the first reaction zone product stream 120) and in the streams exiting the second reaction zone (i.e., the recycle stream 131 and the product stream 132. It should be understood that where more than one product stream exits the second reaction zone 130, the combination of all the product streams exiting the second reaction zone 130 may be referred to as "a sum of the one or more product streams".
In one or more embodiments, the mass flow of the components present in the streams exiting the first reaction zone, which is based on 1 lb. of ethylene produced, includes from greater than or equal to 0.100 lbs. to less than or equal to 0.300 lbs. $C_5H_{12}$, such as about 0.218 lbs. $C_5H_{12}$; from greater than or equal to 0.300 lbs. to less than or equal to 0.500 lbs. $C_4H_{10}$, such as about 0.436 lbs. $C_4H_{10}$; from greater than or equal to 1.300 lbs. to less than or equal to 1.500 lbs. $C_3H_8$, such as about 1.410 lbs. $C_3H_8$; from greater than or equal to 0.750 lbs. to less than or equal to 0.950 lbs. $C_2H_6$, such as about 0.843 lbs. $C_2H_6$; from greater than or equal to 3.200 lbs. to less than or equal to 3.500 lbs. $H_2O$, such as about 3.386 lbs. $H_2O$; and less than or equal to 0.010 lbs. $CO_2$, such as less than 0.005 lbs. $CO_2$, less than 0.001 lbs. $CO_2$, or even no $CO_2$.

In one or more embodiments, the mass flow of the components present in the streams exiting the second reaction zone, which is based on 1 lb. of ethylene produced, includes from greater than or equal to 0.1400 lbs. to less than or equal to 0.1600 lbs. $H_2$, such as about 0.1490 lbs. $H_2$; from greater than or equal to 0.2900 lbs. to less than or equal to 0.3100 lbs. $CH_4$, such as about 0.2971 lbs. $CH_4$; about 1.0000 lbs. $C_2H_4$; from greater than or equal to 1.9000 lbs. to less than or equal to 2.1000 lbs. $C_3H_6$, such as about 1.9900 lbs. $C_3H_6$; from greater than or equal to 0.1200 lbs. to less than or equal to 0.1400 lbs. $C_4H_8$, such as about 0.1317 lbs. $C_4H_8$; from greater than or equal to 0.1000 lbs. to less than or equal to 0.1200 lbs. pygas, such as about 0.1134 lbs. pygas; and from greater than or equal to 0.0165 lbs. to less than or equal to 0.0185 lbs. of other heavy hydrocarbons, such as about 0.0176 lbs. other heavy hydrocarbons.

It should be understood that in various embodiments: (1) fresh ethane (331) may be fed to the cracker in addition to the stream introduced to the cracker from the first reaction zone and no fresh propane (332) may be fed to the PDH reactor; (2) fresh propane (332) may be fed to the PDH reactor in addition to the stream introduced to the cracker from the first reaction zone and no fresh ethane (331) may be fed to the cracker; or (3) fresh ethane (331) may be fed to the cracker in addition to the stream introduced to the cracker from the first reaction zone and fresh propane (332) may be fed to the PDH reactor. Further, in some embodiments, propane (332) may be fed to the cracker alone, or propane (332) may be fed to both the cracker and the PDH reactor.

Embodiments of systems and processes for converting a stream comprising carbon into $C_2$ to $C_5$ hydrocarbons result in improved efficiencies over known processes for converting a stream comprising carbon into $C_2$ to $C_5$ hydrocarbons. For instance, in one or more embodiments, a ratio in lb./lb. of $CH_4$ fed to the system in a feed stream—including any recycled $CH_4$—and $C_2$ to $C_5$ alkanes produced ($CH_4$/alkanes ratio) is less than 1.17, such as less than or equal to 1.15, less than or equal to 1.14, less than or equal to 1.13, or less than or equal to 1.12. For each of the above embodiments, the $CH_4$/alkanes ratio is greater than or equal to 1.00, such as greater than or equal to 1.05, or greater than or equal to 1.10.

Additionally, in some embodiments, a ratio in lb./lb. of $O_2$ fed to the system in a feed stream to $C_2$ to $C_5$ alkanes produced ($O_2$/alkanes ratio) is less than or equal to 1.10, such as less than or equal to 1.08, less than or equal to 1.06, less than or equal to 1.05, or less than or equal to 1.04. For each of the above embodiments, the $O_2$/alkanes ratio is greater than or equal to 1.00, such as greater than or equal to 1.01, or greater than or equal to 1.02.

Further, in various embodiments, the efficiency for converting carbon in $CH_4$ to $C_2$ to $C_5$ alkanes is greater than 0.93, such as greater than or equal to 0.94, greater than or equal to 0.95, greater than or equal to 0.96, greater than or equal to 0.97, greater than or equal to 0.98, or greater than or equal to 0.99.

EXAMPLES

Embodiments will be further clarified by the following examples. The mass balances in the examples provided below may be obtained by a skilled artisan using conventional modelling software, such as, for example, Aspen.

Syngas generation is required for the production of alkanes. The syngas generation process is the same for all cases with the same operating assumptions. Syngas generation is accomplished by feeding methane and water into a reformer. In cases that involve the recycle of methane and $H_2$, this feed will also contain $H_2$.

The feed to the reformer is at 425° C. and the composition if 36 wt % $CH_4$ and 63 wt % water. $H_2$ can also be fed into the reformer with the methane, and the temperature is also 425° C. The reformer pressure is 42 bar.

The reformer outlet is at equilibrium for the following reactions:

$$CH_4 + H_2O = CO + 3H_2 \quad 1)$$

$$CO + H_2O = H_2 + CO_2 \quad 2)$$

The outlet of the reformer is fed to a PDX with oxygen feed where the following reactions occur:

$$CH_4 + 0.5O_2 = CO + 2H_2 \quad 3)$$

$$CH_4 + 2O_2 = CO_2 + 2H_2O \quad 4)$$

Ten percent of the methane that is reacted is assumed to be converted to $CO_2$ and 90 percent is converted to CO. The methane concentration at the PDX outlet is controlled to be 1.5 mol % by the oxygen feed rate. The outlet stream from the PDX supplies the heat to the reformer by being cooled to 450° C. on the reformer shell. Water is removed from the syngas before feeding the alkane production reaction.

Alkane products are produced in the following distribution:

|  | relative moles/hr |
|---|---|
| $3H_2 + CO = CH_4 + H_2O$ | 12.1 |
| $5H_2 + 2CO = C_2H_6 + 2H_2O$ | 34.4 |
| $7H_2 + 3CO = C_3H_8 + 3H_2O$ | 40.4 |
| $9H_2 + 4CO = C_4H_{10} + 4H_2O$ | 9.4 |
| $11H_2 + 5CO = C_5H_{12} + 5H_2O$ | 3.7 |

The reactor product is also in water gas shift equilibrium.

Three reactor stages are used in the simulations. After each reactor stage, water is removed before feeding to the next reactor stage. The CO conversion across all three reactor stages is specified to be 90%. Using three reactor stages in this manner is not essential for the invention: similar results would have been obtained using a single reactor at equal CO conversion level.

The product gas from the reactor is separated into a water stream, a product stream containing $C_2H_6$ and higher carbon products, and a gas stream containing $H_2$, $N_2$, CO, $CO_2$, and $CH_4$. Twenty five percent of this stream is fed back to the reformer to control the $CH_4$ concentration at the reactor inlet at about 6 mol %. About 8 mol % is purged to control the $N_2$ concentration at about 2 mol % at the reactor inlet. $N_2$ is assumed to enter the process in the $CH_4$ feed gas at 1 mol %. For the remaining gas, a portion of the $CO_2$ is removed and the remainder of the gas is recycled to the reactor. The $CO_2$ removal is used to control the reactor inlet concentration at about 12 mol % $CO_2$.

The alkane products are converted to olefins by conventional steam cracking, or a combination of steam cracking and propane dehydrogenation. The assumptions on cracking efficiency for each feed component are given in Table 1 below:

TABLE 1

| | Feed component | | | | | | | |
|---|---|---|---|---|---|---|---|---|
| | ethylene | propylene | $C_4$ | pygas | heavies | fuel, $CH_4$ | fuel, $H_2$ | $C_2H_6$ |
| ethane | 77.2 | 2.1 | 2.9 | 2.9 | 0.4 | 7.6 | 5.6 | |
| propane | 44.1 | 16.6 | 4.3 | 5.1 | 0.6 | 26.3 | 1.7 | |
| butane | 38.8 | 19.5 | 15.9 | 4.3 | 0.3 | 19.2 | 0.8 | |
| pentane | 29.3 | 14.4 | 9.3 | 22.7 | 5.7 | 16.4 | 0.9 | |
| PDH | 0.616 | 83.1 | 0.62 | 0.757 | | 4.65 | 3.97 | 5.94 |

Product composition from cracking in weight percent.

Example 1

Example 1 is a simulation of the conversion of a carbon-containing stream to $C_2$ to $C_5$ hydrocarbons according to embodiments depicted in FIG. 1. In particular, a feed stream comprising $CH_4$ and $O_2$ is fed to a first reaction zone comprising an alkane production unit. The mass flow of the feed stream, based on the production of 1 lb. of ethylene, is 1.076 lbs. $CH_4$ and 1.238 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 0.005 lbs. $CO_2$, 1.370 lbs. $H_2O$, 0.342 lbs. $C_2H_6$, 0.571 lbs. $C_3H_8$, 0.177 lbs. $C_4H_{10}$, and 0.088 lbs. $C_5H_{12}$.

The $C_2H_6$, $C_3H_8$, $C_4H_{10}$, and $C_5H_{12}$ produced in the first reaction zone are fed along with a feed of additional fresh ethane to a second reaction zone comprising a conventional cracker, which produces $C_2$ to $C_5$ olefins. The fresh ethane makes up 30 wt % of the feed to the cracker. The mass flow of the fresh ethane, based on the production of 1 lb. of ethylene, is 0.505 lbs.

The second reaction zone product stream comprises $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.0598 lbs. $H_2$, 0.2626 lbs. $CH_4$, 1.0000 lbs. $C_2H_4$, 0.1598 lbs. $C_3H_6$, 0.0854 lbs. $C_4H_8$, 0.0813 lbs. pygas, and 0.0124 lbs. of other heavy hydrocarbons.

The $CH_4$ and $H_2$ in the second reaction zone product stream are recycled back to the first reaction zone. The additional hydrogen improves the carbon efficiency of the methane to alkane process which results in a reduced amount of fresh methane in the feed stream, a lower oxygen feed requirement and essentially no $CO_2$ removal from the process, resulting in the highest natural gas efficiency. Some $CO_2$ is removed in an inert gas purge which is used to control $N_2$ and $CH_4$ concentration at the reactor inlet. But, a separate $CO_2$ removal system is not required.

The $CH_4$/alkanes ratio of Example 1 is 1.14; the $O_2$/alkanes ratio of Example 1 is 1.05; and the carbon efficiency of Example 1 is 0.96.

Example 2

Example 2 is a simulation of the conversion of a carbon-containing stream to $C_2$ to $C_5$ hydrocarbons according to embodiments depicted in FIG. 2A. In particular, a feed stream comprising $CH_4$ and $O_2$ is fed to a first reaction zone comprising an alkane production unit. The mass flow of the feed stream, based on the production of 1 lb. of ethylene, is 2.093 lbs. $CH_4$ and 2.129 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 0.003 lbs. $CO_2$, 2.360 lbs. $H_2O$, 0.588 lbs. $C_2H_6$, 0.984 lbs. $C_3H_8$, 0.304 lbs. $C_4H_{10}$, and 0.152 lbs. $C_5H_{12}$.

The $C_2H_6$, $C_3H_8$, $C_4H_{10}$, and $C_5H_{12}$ produced in the first reaction zone are fed to a second reaction zone. The $C_2H_6$, $C_4H_{10}$, and $C_5H_{12}$ produced in the first reaction zone are fed along with a feed of additional fresh ethane to a conventional cracker, which produces $C_2H_4$, $C_3H_6$, $C_4H_8$, and $C_5H_{10}$ olefins. The $C_3H_8$ produced in the first reaction zone is fed to a conventional PDH reactor, which produces $C_3H_6$. The fresh ethane makes up 17.5 wt % of the feed to the cracker. The mass flow of the fresh ethane, based on the production of 1 lb. of ethylene, is 0.430 lbs.

The outlet streams from the cracker and the PDH reactor are combined into a second reaction zone product stream comprising $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.1036 lbs. $H_2$, 0.2106 lbs. $CH_4$, 1.0000 lbs. $C_2H_4$, 0.9212 lbs. $C_3H_6$, 0.0998 lbs. $C_4H_8$, 0.0863 lbs. pygas, and 0.0139 lbs. of other heavy hydrocarbons.

The $CH_4$ and $H_2$ in the second reaction zone product stream are recycled back to the first reaction zone. The additional hydrogen improves the carbon efficiency of the methane to alkane process which results in a reduced amount of fresh methane in the feed stream, a lower oxygen feed requirement and essentially no $CO_2$ removal from the process, resulting in the highest natural gas efficiency. Some $CO_2$ is removed in an inert gas purge which is used to control $N_2$ and $CH_4$ concentration at the reactor inlet. But, a separate $CO_2$ removal system is not required.

The $CH_4$/alkanes ratio of Example 2 is 1.14; the $O_2$/alkanes ratio of Example 2 is 1.05; and the carbon efficiency of Example 2 is 0.96.

Example 3

Example 3 is a simulation of the conversion of a carbon-containing stream to $C_2$ to $C_5$ hydrocarbons according to embodiments depicted in FIG. 2B. In particular, a feed stream comprising $CH_4$ and $O_2$ is fed to a first reaction zone comprising an alkane production unit. The mass flow of the feed stream, based on the production of 1 lb. of ethylene, is 3.003 lbs. $CH_4$ and 3.051 lbs. $O_2$.

The first reaction zone product stream comprises $H_2O$, $C_2H_6$, $C_3H_8$, $C_4H_{10}$, and $C_5H_{12}$. There is no $CO_2$ in the first reaction zone product stream. The $H_2O$ is separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 3.386 lbs. $H_2O$, 0.843 lbs. $C_2H_6$, 1.410 lbs. $C_3H_8$, 0.436 lbs. $C_4H_{10}$, and 0.218 lbs. $C_5H_{12}$.

The $C_2H_6$, $C_3H_8$, $C_4H_{10}$, and $C_5H_{12}$ produced in the first reaction zone are fed to a second reaction zone. The $C_2H_6$, $C_4H_{10}$, and $C_5H_{12}$ produced in the first reaction zone are fed along to a conventional cracker, which produces $C_2H_4$, $C_3H_6$, $C_4H_8$, and $C_5H_{10}$ olefins. The $C_3H_8$ produced in the first reaction zone is fed along with a fresh feed of propane to a conventional PDH reactor, which produces $C_3H_6$. The fresh propane makes up 22 wt % of the feed to the PDH reactor. The mass flow of the fresh propane, based on the production of 1 lb. of ethylene, is 0.820 lbs.

The outlet streams from the cracker and the PDH reactor are combined into a second reaction zone product stream comprising $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.1490 lbs. $H_2$, 0.2971 lbs. $CH_4$, 1.0000 lbs. $C_2H_4$, 1.9900 lbs. $C_3H_6$, 0.1317 lbs. $C_4H_8$, 0.1134 lbs. pygas, and 0.0176 lbs. of other heavy hydrocarbons.

The $CH_4$ and $H_2$ in the second reaction zone product stream are recycled back to the first reaction zone. The additional hydrogen improves the carbon efficiency of the methane to alkane process which results in a reduced amount of fresh methane in the feed stream, a lower oxygen feed requirement and no $CO_2$ removal from the process, resulting in the highest natural gas efficiency.

The $CH_4$/alkanes ratio of Example 3 is 1.14; the $O_2$/alkanes ratio of Example 3 is 1.05; and the carbon efficiency of Example 3 is 0.96.

Comparative Example 1

Comparative Example 1 is a simulation similar to Example 1, but no fresh ethane is fed to the cracker and hydrogen is not recycled back to the first reaction zone.

In particular, a feed stream comprising $CH_4$ and $O_2$ is fed to a first reaction zone comprising an alkane production unit. The mass flow of the feed stream, based on the production of 1 lb. of ethylene, is 2.47 lbs. $CH_4$ and 2.25 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 0.688 lbs. $CO_2$, 1.922 lbs. $H_2O$, 0.560 lbs. $C_2H_6$, 0.936 lbs. $C_3H_8$, 0.290 lbs. $C_4H_{10}$, and 0.145 lbs. $C_5H_{12}$.

The $C_2H_6$, $C_3H_8$, $C_4H_{10}$, and $C_5H_{12}$ produced in the first reaction zone are fed to a second reaction zone comprising a conventional cracker, which produces $C_2$ to $C_5$ olefins.

The second reaction zone product stream comprises $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.0513 lbs. $H_2$, 0.3677 lbs. $CH_4$, 1.0000 lbs. $C_2H_4$, 0.2445 lbs. $C_3H_6$, 0.1160 lbs. $C_4H_8$, 0.1093 lbs. pygas, and 0.0170 lbs. of other heavy hydrocarbons.

The $CH_4$/alkanes ratio of Comparative Example 1 is 1.28; the $O_2$/alkanes ratio of Comparative Example 1 is 1.17; and the carbon efficiency of Comparative Example 1 is 0.85.

Comparative Example 2

Comparative Example 2 is a simulation similar to Example 2, but no fresh ethane is fed to the cracker and hydrogen is not recycled back to the first reaction zone.

In particular, a feed stream comprising $CH_4$ and $O_2$ is fed to a first reaction zone comprising an alkane production unit. The mass flow of the feed stream, based on the production of 1 lb. of ethylene, is 3.88 lbs. $CH_4$ and 3.54 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 1.083 lbs. $CO_2$, 3.024 lbs. $H_2O$, 0.881 lbs. $C_2H_6$, 1.473 lbs. $C_3H_8$, 0.456 lbs. $C_4H_{10}$, and 0.228 lbs. $C_5H_{12}$.

The $C_2H_6$, $C_3H_8$, $C_4H_{10}$, and $C_5H_{12}$ produced in the first reaction zone are fed to a second reaction zone. The $C_2H_6$, $C_4H_{10}$, and $C_5H_{12}$ produced in the first reaction zone are fed to a conventional cracker, which produces $C_2H_4$, $C_3H_6$, $C_4H_8$, and $C_5H_{10}$ olefins. The $C_3H_8$ produced in the first reaction zone is fed to a conventional PDH reactor, which produces $C_3H_6$.

The outlet streams from the cracker and the PDH reactor are combined into a second reaction zone product stream comprising $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.1188 lbs. $H_2$, 0.2666 lbs. $CH_4$, 1.0000 lbs. $C_2H_4$, 1.3659 lbs. $C_3H_6$, 0.1308 lbs. $C_4H_8$, 0.1105 lbs. pygas, and 0.0182 lbs. of other heavy hydrocarbons.

The $CH_4$/alkanes ratio of Comparative Example 2 is 1.28; the $O_2$/alkanes ratio of Comparative Example 2 is 1.17; and the carbon efficiency of Comparative Example 2 is 0.85.

Comparative Example 3

Comparative Example 3 is a simulation similar to Example 1, but no fresh ethane is fed to the cracker.

A feed stream comprising $CH_4$ and $O_2$ is fed to a first reaction zone comprising an alkane production unit. The mass flow of the feed stream, based on the production of 1 lb. of ethylene, is 1.965 lbs. $CH_4$ and 2.142 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 0.353 lbs. $CO_2$, 2.081 lbs. $H_2O$, 0.560 lbs. $C_2H_6$, 0.936 lbs. $C_3H_8$, 0.290 lbs. $C_4H_{10}$, and 0.145 lbs. $C_5H_{12}$.

The $C_2H_6$, $C_3H_8$, $C_4H_{10}$, and $C_5H_{12}$ produced in the first reaction zone are fed to a second reaction zone comprising a conventional cracker, which produces $C_2$ to $C_5$ olefins.

The second reaction zone product stream comprises $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.0513 lbs. $H_2$, 0.3677 lbs. $CH_4$, 1.0000 lbs. $C_2H_4$, 0.2445 lbs. $C_3H_6$, 0.1160 lbs. $C_4H_8$, 0.1093 lbs. pygas, and 0.0170 lbs. of other heavy hydrocarbons.

The $CH_4$ and $H_2$ in the second reaction zone product stream are recycled back to the first reaction zone. However, a high amount of $CO_2$ is still produced in the first reaction zone. Accordingly, this process does not efficiently convert carbon in the feed stream to $C_2$ to $C_5$ hydrocarbons, and a separate $CO_2$ removal system is required.

The $CH_4$/alkanes ratio of Comparative Example 3 is 1.21; the $O_2$/alkanes ratio of Comparative Example 3 is 1.11; and the carbon efficiency of Comparative Example 3 is 0.90.

Comparative Example 4

Comparative Example 4 is similar to Example 2, but no fresh ethane is fed to the cracker.

A feed stream comprising $CH_4$ and $O_2$ is fed to a first reaction zone comprising an alkane production unit. The mass flow of the feed stream, based on the production of 1 lb. of ethylene, is 3.294 lbs. $CH_4$ and 3.280 lbs. $O_2$.

The first reaction zone product stream comprises $CO_2$, $H_2O$, $C_2H_6$, $C_3H_8$, $C_4H_{10}$, and $C_5H_{12}$. The $CO_2$ and $H_2O$ are separated from the remaining components (i.e., $C_2H_6$, $C_3H_8$, $C_4H_{10}$, and $C_5H_{12}$) and discarded. The mass flow of the first reaction zone product stream, based on the production of 1 lb. of ethylene, is 0.283 lbs. $CO_2$, 3.402 lbs. $H_2O$, 0.881 lbs. $C_2H_6$, 1.473 lbs. $C_3H_8$, 0.456 lbs. $C_4H_{10}$, and 0.228 lbs. $C_5H_{12}$.

The $C_2H_6$, $C_3H_8$, $C_4H_{10}$, and $C_5H_{12}$ produced in the first reaction zone are fed to a second reaction zone. The $C_2H_6$, $C_4H_{10}$, and $C_5H_{12}$ produced in the first reaction zone are fed to a conventional cracker, which produces $C_2H_4$, $C_3H_6$, $C_4H_8$, and $C_5H_{10}$ olefins. The $C_3H_8$ produced in the first reaction zone is fed to a conventional PDH reactor, which produces $C_3H_6$.

The outlet streams from the cracker and the PDH reactor are combined into a second reaction zone product stream comprising $H_2$, $CH_4$, $C_2H_4$, $C_3H_6$, $C_4H_8$, pygas, and other heavy hydrocarbons. The mass flow of the second reaction zone product stream, based on the production of 1 lb. of ethylene, is 0.1188 lbs. $H_2$, 0.2666 lbs. $CH_4$, 1.0000 lbs. $C_2H_4$, 1.3659 lbs. $C_3H_6$, 0.1308 lbs. $C_4H_8$, 0.1105 lbs. pygas, and 0.0182 lbs. of other heavy hydrocarbons.

The $CH_4$ and $H_2$ in the second reaction zone product stream are recycled back to the first reaction zone. However, a high amount of $CO_2$ is still produced in the first reaction zone. Accordingly, this process does not efficiently convert carbon in the feed stream to $C_2$ to $C_5$ hydrocarbons, and a separate $CO_2$ removal system is required.

The $CH_4$/alkanes ratio of Comparative Example 4 is 1.17; the $O_2$/alkanes ratio of Comparative Example 4 is 1.08; and the carbon efficiency of Comparative Example 4 is 0.93.

Example 1 illustrates an improvement over Comparative Example 3, while Examples 2 and 3 illustrate an improvement over Comparative Example 4, which is shown by the elimination of the $CO_2$ removal requirement from the first reaction zone, and by reducing the $O_2$/alkanes ratio. Example 1 uses a small fresh ethane feed to the cracker, Example 2 uses a small fresh ethane feed to the cracker, and Example 3 uses a small fresh propane feed to the PDH unit.

These examples illustrate several options for adding fresh ethane and/or fresh propane feed along with the feed produced from the first reaction zone so that the hydrogen produced from olefins production can be recycled back to the first reaction zone and reduce or eliminate the net removal of $CO_2$ from the process. These examples illustrate various options, but do not include all possible options.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for converting a feed stream comprising carbon to $C_2$ to $C_5$ olefins, comprising:
   introducing a feed stream comprising methane and oxygen to a first reaction zone;
   reacting the methane and oxygen in the first reaction zone to form a first reaction zone product stream comprising a mixture of $C_2$ to $C_5$ alkanes;
   transporting the mixture of $C_2$ to $C_5$ alkanes to a second reaction zone;
   introducing a fresh stream of at least one of ethane and propane to the second reaction zone;
   converting the mixture of $C_2$ to $C_5$ alkanes to $C_2$ to $C_5$ olefins in the second reaction zone;
   producing one or more product streams in the second reaction zone, wherein a sum of the one or more product streams comprises $C_2$ to $C_5$ olefins; and
   producing a recycle stream comprising hydrogen in the second reaction zone, wherein the recycle stream is transported directly from the second reaction zone to the first reaction zone.

2. The process of claim 1, wherein the second reaction zone comprises a cracker.

3. The process of claim 2, wherein introducing a fresh stream of at least one of ethane and propane to the second reaction zone comprises introducing a fresh stream of ethane into the cracker.

4. The process of claim 2, wherein the second reaction zone comprises a propane dehydrogenation reactor.

5. The process of claim 4, wherein introducing a fresh stream of at least one of ethane and propane to the second reaction zone comprises introducing propane into the propane dehydrogenation reactor.

6. The process of claim 5, wherein the second reaction zone comprises a cracker and introducing a fresh stream of at least one of ethane and propane to the second reaction zone comprises introducing propane into the propane dehydrogenation reactor and introducing ethane to the cracker.

7. The process of claim 1, wherein the recycle stream further comprises methane.

8. The process of claim 1, wherein the first reaction zone product stream does not comprise carbon dioxide.

9. The process of claim 1, wherein the first reaction zone comprises a hybrid catalyst.

10. The process of claim 9, wherein the hybrid catalyst comprises a methanol synthesis component and a solid microporous acid component having 8-MR access.

11. The process of claim 1, wherein a $CH_4$/alkanes ratio is less than 1.17.

12. The process of claim 1, wherein a $CH_4$/alkanes ratio is less than or equal to 1.14.

13. The process of claim 1, wherein an $O_2$/alkanes ratio is less than or equal to 1.10.

14. The process of claim 1, wherein a carbon efficiency is greater than 0.93.

15. The process of claim 1, wherein a carbon efficiency is greater than or equal to 0.96.

16. The process of claim 1, wherein the first reaction zone comprises a reformer, a partial oxidation reactor, and a hybrid reactor, wherein the outlet stream of the reformer is introduced into the partial oxidation reactor, and wherein the outlet stream of the partial oxidation reactor is introduced to a hybrid reactor where the outlet stream from the partial oxidation reactor contacts a hybrid catalyst, and wherein the hybrid catalyst converts syngas into oxygenated hydrocarbons and the oxygenated hydrocarbons into $C_2$ to $C_5$ alkanes.

* * * * *